United States Patent [19]

Kaneko

[11] Patent Number: 4,572,671

[45] Date of Patent: Feb. 25, 1986

[54] DENSITOMETER FOR AN ELECTROPHORESIS APPARATUS

[75] Inventor: Nobutaka Kaneko, Hachioji, Japan

[73] Assignee: Olympus Optical Co., Ltd., Tokyo, Japan

[21] Appl. No.: 514,296

[22] Filed: Jul. 15, 1983

[30] Foreign Application Priority Data

Jul. 20, 1982 [JP] Japan .................. 57-126278

[51] Int. Cl.⁴ .......................... G01N 21/00
[52] U.S. Cl. .................. 356/444; 356/244; 356/344
[58] Field of Search ............ 356/444, 344, 244

[56] References Cited

U.S. PATENT DOCUMENTS 3,994,593 11/1976 Kato et al. .................. 356/444
4,204,767 5/1980 Kato et al. .................. 356/444
4,332,472 6/1982 Kato et al. .................. 356/344

Primary Examiner—Bernard D. Pianalto
Attorney, Agent, or Firm—Louis Weinstein

[57] ABSTRACT

A densitometer comprises a first carrier supporter for supporting a carrier formed of a cellulose acetate film for carrying a blood serum specimen after an electrophoresis process is completed and a second carrier supporter for supporting a carrier for a blood serum which is formed of a gel or the like and reinforced with a transparent plate. The first and second carrier supporters are disposed between a light projector and a light receiver in such a manner that the density measurement of fractionated patterns of a blood serum may be effected upon occasion by supporting either the carrier formed of a cellulose acetate film or the carrier formed of a gel or the like.

11 Claims, 9 Drawing Figures

FIG. 2
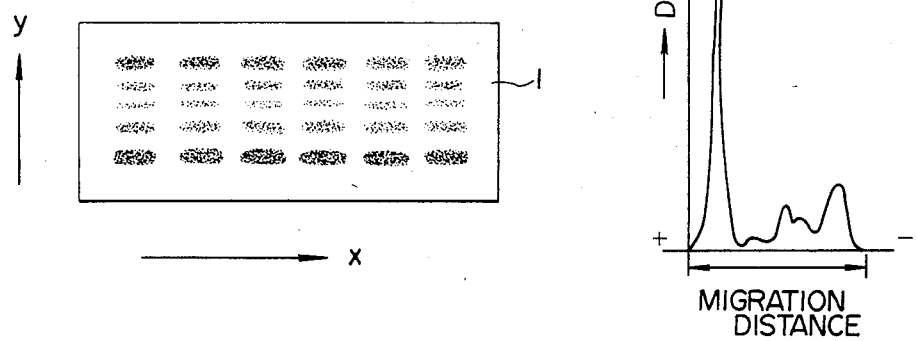
FIG. 3
FIG. 4
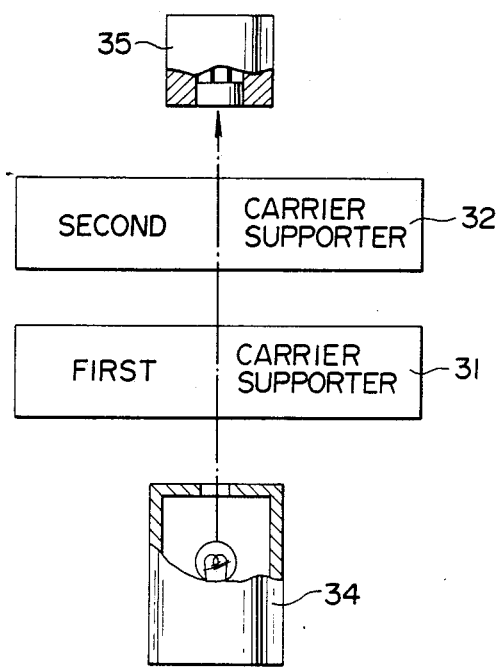

DENSITOMETER FOR AN ELECTROPHORESIS APPARATUS

BACKGROUND OF THE INVENTION

The present invention relates to a densitometer for an electrophoresis apparatus which permits an examination of a blood serum specimen by electrophoretic process.

An electrophoresis apparatus is employed for the determination of protein contained in a blood serum as in hospitals. The general arrangement of the electrophoresis apparatus, referring to FIG. 1, will be explained as follows. A carrier 1 for a blood serum which may be formed of cellulose acetate film and wound into a roll is drawn out by a pair of rollers 2 and is cut to a given length by a cutter 3 which comprises a stationary and a rotating blade. The carrier 1 thus cut off is fed to a buffer solution vessel 4 to be immersed in a buffer solution and then is fed to a blood serum applicator 5 which applies a blood serum, by a conveyor 5a. The blood serum applicator 5 is provided with an application station 5b where a plurality of application members are arranged in rectilinear form along the direction of movement of the carrier 1. A blood serum, a specimen to be examined, is applied onto the carrier 1 at the application station 5b. The blood serum is contained in a serum dish assembly 5c which is disposed at a position directed to the application station 5b. The blood serum applicator 5 further includes a rinsing vessel 5d and a drip device 5e. After applied with a blood serum, the carrier 1 is fed to an electrophoresis station 6 which includes a film conveyor 6a and an electrophoresis compartment 6b. At the electrophoresis station 6, a d.c. voltage is applied to both ends of the carrier 1 in the direction y (perpendicular to paper) which is also perpendicular to the direction x along which the carrier 1 is coveyed. As a result of the energization of carrier 1, protein components such as albumin, $\alpha$, $\beta$, $\gamma$-globulin are fractionated in the direction y in accordance with their respective mobilities and the resulted fractionated patterns are formed as shown in FIG. 2, for example. The carrier 1 carrying the fractionated patterns thereon is supplied to a dyeing unit 7a, a decolorizing unit 7b and a drying unit 7c. The carrier 1 is finally fed to a densitometer 10.

The densitometer 10 comprises a clearing liquid vessel 12 which contains a clearing liquid 11 for rendering the carrier 1 for a blood serum which is formed of cellulose acetate film clear, a plurality of pairs of rollers $13a_1$, $13b_1$ to $13a_4$, $13b_4$ (four pairs shown in FIG. 1) as a carrier supporting member which is disposed within the clearing liquid vessel 12, a photometry unit which comprises a light projector 14 and a light receiver 15 between which the bottom of the clearing liquid vessel 12 is disposed and a cover 16 for preventing outside light from entering. The projector 14 comprises a lamp 17, a condenser lens 18 and a perforated member 19. The receiver 15 comprises a photoelectric transducer 20. A transparent plate 21 such as a glass plate is provided in the middle of the bottom of clearing liquid vessel 12. The light incident surface of the receiver 15 is immersed in the clearing liquid vessel 11 so as not to be subject to a disturbance such as turbulence of the surface of the clearing liquid 11.

When the carrier 1 carrying a blood serum is fed into the densitometer 10, the film is immersed in the clearing liquid 11 to render it clear and only fractionated patterns of a blood serum on the carrier 1 clearly appear. The carrier 1 is then fed between the projector 14 and the receiver 15 where the receiver 15 detects light which is emitted from the projector 14 and passes through the carrier film. As such, the fractionated patterns are measured as a variation in density in accordance with a shade of color for impression of electrophoresis on the carrier 1. While in the density measurement with the densitometer 10, the carrier 1 is positioned in the direction x shown in FIG. 2 by means of rollers $13a_1$, $13b_1$ through $13a_4$, $13b_4$ in such a manner that the center of fractionated patterns of each blood serum coincides with the center of a photometric spot and then the measurement is effected by scanning both the projector 14 and the receiver 15 in the direction y shown in FIG. 2. During the scanning in the direction y, the receiver 15 produces an output in accordance with a distribution of variation in density and thus a quantitative and qualitative analysis of protein in a blood serum is effected with the distribution of variation in density. The scanning in the direction y is successively conducted whenever positioning of each carrier carrying a specimen to be examined at a pitch for each blood serum in the direction x is terminated and the above-mentioned operation is successively repeated to measure density of fractionated patterns for all blood serums on the carriers 1 which have been cut to a given length.

The conventional densitometer 10 described above is able to effect a measurement only for a carrier film carrying a blood serum which is formed of a cellulose acetate film but is unable to do so for a carrier film other than this. As a carrier for a blood serum other than the carrier 1 formed of a cellulose acetate film, an agar, starch, polyacrylic amide-gel film or the like is typical. These gel films are much thicker than the cellulose acetate film, specifically about 1 mm thick compared with 0.1 to 0.15 mm thick of the latter film and is weak in strength so that most of these films may be reinforced by placing them on a glass or a plastic plate. When the measurement is conducted using such a gel carrier reinforced by a glass plate with the conventional densitometer 10 shown in FIG. 1, it is impossible to feed the gel carrier by means of rollers $13a_1$, $13b_1$ to $13a_4$, $13b_4$ since the rigid plate does not curve therearound. Even if a plastic plate for reinforcing a gel carrier film is used by thinning it so as to easily curve around the rollers, the gel layer is disadvantageously too thick to peel from the plastic plate and may be damaged by being caught between the rollers during conveying with the rollers. To eliminate this disadvantage, the following idea occurs that the upper rollers $13a_1$ to $13a_4$ among the four pairs of rollers $13a_1$, $13b_1$ to $13a_4$, $13b_4$ and the light receiver 15 are constructed to be integral with the cover 16 in such a manner that they are integrally removable and after a gel carrier is placed on the transparent plate 21 the cover 16 in integral with rollers $13a_1$ to $13a_4$ and receiver 15 which have been removed are again placed in position to effect the density measurement of fractionated patterns. However, this requires much time and labor in the measurement. At this time, since the gel carrier need not be immersed in the clearing liquid 11, the latter must be removed from the vessel 12 or the measurement is effected in the clearing liquid 11 which is left as it is and thereafter clearing liquid adhered to the carrier must be removed. Consequently, the density measurement of fractionated patterns for proteins of a blood serum which are formed on the gel carrier requires much time so that it will be difficult to effect a rapid analysis.

SUMMARY OF THE INVENTION

In view of the foregoing disadvantages of the conventional densitometer, it is an object of the invention to provide a densitometer which is provided with a plurality of carrier supporters for supporting respective carriers formed of various kinds of material for a blood serum between a light projector and a light receiver.

According to the invention, the densitometer is adapted to support different kinds of carriers for a blood serum which are formed of, for example, a cellulose acetate film or gels and to conduct the density measurement of fractionated patterns after the electrophoresis process for each carrier. Consequently, by way of example, when a measurement using a first carrier which differs from a second carrier which is normally used with an electrophoresis apparatus is required while an automatic analysis is conducted with the apparatus, the first carrier may be supported by suspending the conduct of the automatic analysis. Thus, it is possible easily to conduct the density measurement of fractionated patterns for proteins of a blood serum.

BRIEF DESCRIPTION OF THE DRAWINGS

FIG. 2 is a plan view of fractionated patterns after an electrophoresis process is achieved for a carrier for a blood serum which is formed of a cellulose acetate film in general use;

FIG. 3 is a graph illustrating the result of analysis for a blood serum on the carrier;

FIG. 4 is a schematic view of a basic construction of the densitometer according to the invention;

DETAILED DESCRIPTION OF PREFERRED EMBODIMENTS

Referring to FIG. 4, there is shown a basic construction of a densitometer according to the invention. The densitometer comprises a first carrier supporter 31 for supporting a carrier formed of a cellulose acetate film and a second carrier supporter 32 for supporting a carrier formed of a gel or the like, both of which are disposed between a light projector 34 and a light receiver 35. By way of example, two carrier supporters are shown in FIG. 4. If necessary, however, a plurality of carrier supporters, three and over, may be arranged. These carrier supporters may be constructed so that each of them may be optimum for a particular carrier to be measured.

Figure 5:
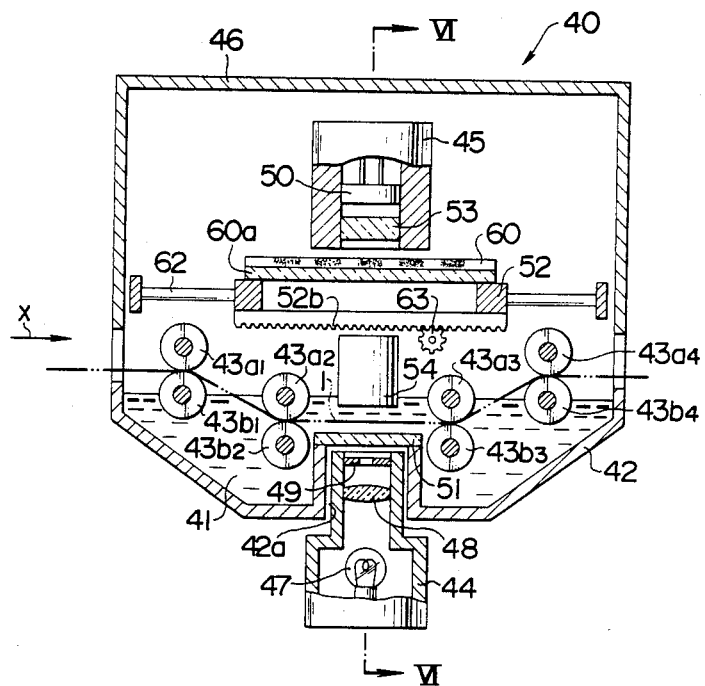
FIG. 5 is a cross section of the densitometer according to one embodiment of the invention.
Figure 6:
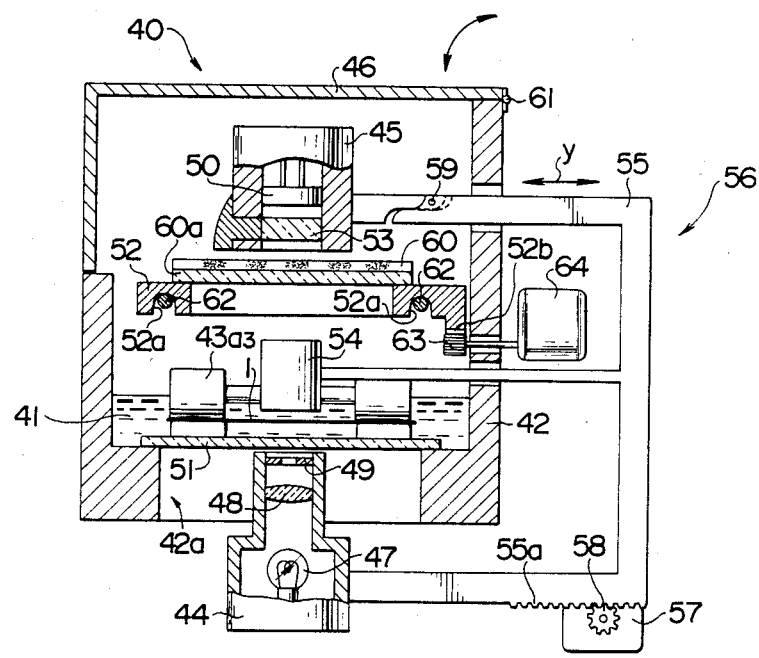
FIG. 6 is a cross section taken along the line VI—VI shown in FIG. 5.

Referring now to FIGS. 5 and 6, the densitometer 40 comprises a clearing liquid vessel 42 which contains a clearing liquid 41, a plurality of pairs of rollers $43a_1$, $43b_1$ to $43a_4$, $43b_4$ (collectively referred to as rollers 43) provided for the first carrier supporter 31 (see FIG. 4), a support rest 52 provided for the second carrier supporter 32 (see FIG. 4), a light projector 44 disposed under the bottom center of the clearing liquid vessel 42, a light receiver 45 which is disposed above the vessel 42 and is directed to the projector 44 and a cover 46 which covers all of the internal members for preventing outside light from entering into the vessel 42. A transfer path with rollers 43 and a transfer path with the support rest 52 are arranged between the projector 44 and the receiver 45. The projector 44 comprises a lamp 47, a condenser lens 48 and a perforated plate 49. The receiver 45 comprises a photoelectric transducer 50 and a filter 53 which is removably mounted on the body of receiver 50. A guide recess 42a for scanning movement of the projector 44 is formed in the bottom center of the clearing liquid vessel 42. The ceiling of recess 42a, namely, the portion facing to the perforated plate 49, is formed of a transparent plate 51 such as a glass plate so that light from the projector 44 may pass therethrough. A light flux transmitter 54 is disposed between the respective transfer paths formed of rollers 43 and formed of support rest 52. The light flux transmitter 54 has its optical axis in coincidence with the optical axes of the projector 44 and the receiver 45 and is arranged in such a manner that its lower portion is securely immersed in the clearing liquid 41. With the lower portion of the light flux transmitter 54 being immersed in the clearing liquid, the transmitter 54 prevents light flux from curving due to disturbance of the liquid surface. The transmitter 54, the projector 44 and the receiver 45 are integrally connected by a frame 55 to form a photometry unit 56. The frame 55 has a rack 55a on its lower part. The rack 55a engages with a pinion 58 which is in integral with a drive shaft of a motor 57 so that the photometry unit 56 including projector 44, receiver 45 and transmitter 54 can be driven in the direction y for scanning and detecting fractionated patterns of a blood serum by driving the motor 57. The receiver 45 and the frame 55 are connected by a pivot pin 59 so that the receiver 45 is rotatable with relation to the frame 55 in such a manner that a carrier formed of a gel 60 is easily taken in and out in order to be mounted on or removed from a support rest 52 which is below the receiver 45. Similarly, the cover 46 is rotatably attached to the clearing liquid vessel 42 by means of a hinge 61.

The support rest 52 is provided to mount the gel carrier 60 which is reinforced with a reinforced plate 60a made of transparent glass or a plastic material, the central part of which has an opening at least over the extent opposing to fractionated patterns which are formed on the gel carrier 60, such that a plan view of the support rest 52 forms a picture frame. The support rest 52 is horizontally mounted on two guide rails 62 which are disposed along the same direction x as the transfer direction of the carrier film 1 moved by means of rollers 43 in such a condition that guide rails 62 engage with guide grooves 52a. The support rest 52 has a rack 52b which is formed on the lower surface to one side of one of the guide grooves 52a. A pinion 63 is integral with a drive shaft of a motor 64 at a place facing the rack 52b. As a result, the support rest 52 may be easily removed and remounted. Specifically, the rack 52b engages the pinion 63 only by mounting the support rest 52 on the guide rail 62 so that when motor 64 is driven the support rest 52 may be moved on the guide rail 62 in the direction x. Alternatively, the support rest 52 may be slidably constructed on guide rails 62 so as not to come off therefrom.

Figure 1:
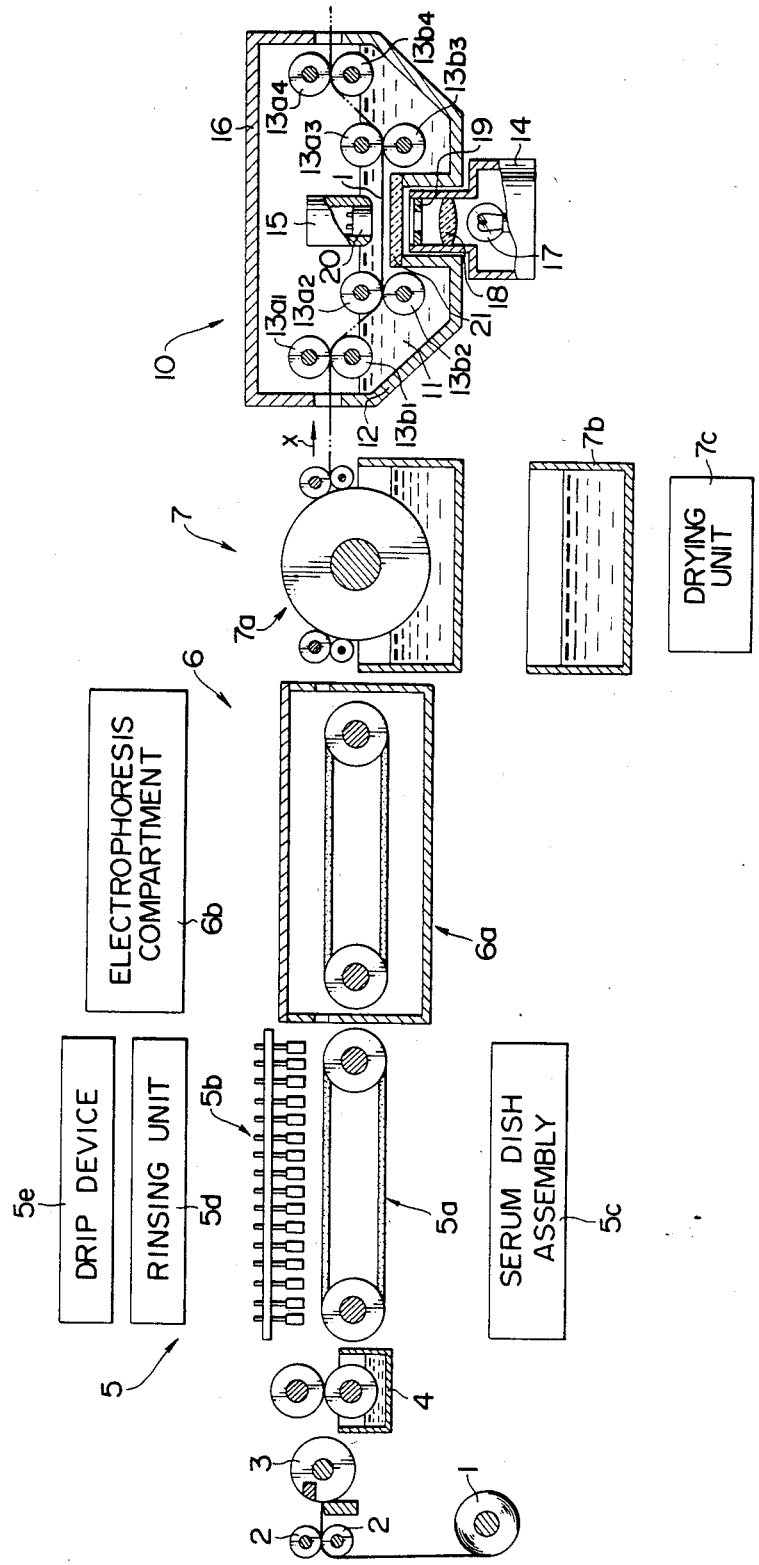
FIG. 1 is a schematic view of the general arrangement of an electrophoresis apparatus according to one embodiment of the invention.

In operation, a cellulose acetate carrier film 1 carrying a blood serum to be examined which has gone through process steps of wetting, blood serum application, electrophoresis, dyeing, decolorizing and drying with an electrophoresis apparatus (FIG. 1) in a similar manner as in a conventional case, is fed to the densitometer 40. The carrier 1 is caught between roller $43a_1$ and roller $43b_1$ to be introduced into the clearing liquid vessel 42 and is further caught between roller $42a_2$ and roller $43b_2$ to be immersed in clearing liquid 41. A guide member (not shown) is provided between roller pairs so that the carrier 1 may be securely fed to the next roller pair. When immersed in clearing liquid 41, the carrier film 1 becomes transparent. The cleared carrier film 1 is further fed in the direction x to be caught between rollers $43a_3$ and $43b_3$ and the center position of fractionated patterns is detected by a specimen detection means (not shown). Thus, the carrier 1 is temporarily stopped in such a condition that it is held between roller pair $43a_2$, $43b_2$ and roller pair $43a_3$, $43b_3$ so that the center of the fractionated patterns may coincide with the optical axis of projector 44-receiver 45. Subsequently, motor 57 is driven and the photometry apparatus 56 including projector 44, receiver 45 and light flux transmitter 54 scans in the direction y to detect the density distribution of one specimen blood serum on the carrier 1. When the density measurement of the one specimen blood serum is finished, the carrier 1 is scanned in the direction x by rollers 43 and stops at a measurement station of the next specimen where the carrier 1 is scanned in the direction y by the photometry apparatus 56, in a manner similar to that described above. Thus, the measurement of each specimen on the carrier 1 is successively conducted. Upon completion of the measurement, the carrier 1 is fed from rollers $43a_3$, $43b_3$ to rollers $43a_4$, $43b_4$ and is drawn out from clearing liquid 41 to be transferred to the exterior of the densitometer 40. Thereafter, the densitometer 40 into which the next blood serum carrier is introduced for the measurement thereof operates in a manner similar to that described above.

The foregoing is the operation of the densitometer during the automatic analysis, during which the carrier 1 is measured by the photometry apparatus 56 and a gel carrier 60 for a blood serum is not mounted on the support rest 52 which is the second carrier supporter. Therefore, the support rest 52 may be removed during the automatic analysis.

In the following, an operation for the density measurement of fractionated patterns for the gel carrier 60 reinforced with a reinforcing plate 60a, which carrier is unable to be fed by being caught between rollers 43, will be described. After ensuring that a cellulose acetate carrier 1 does not exist within the densitometer 40, the cover 46 is opened and filter 53 having the optimum wavelength for an analysis item of density measurement is set on light receiver 45. Then, light receiver 45 is turned around pivot pin 59 by lifting it to move receiver 45 away from support rest 52. A gel carrier 60 is set on support rest 52 and light receiver 45 is again returned to close cover 46. Since specimens are applied to the gel carrier 60 at regular intervals in a manner similar to the carrier film 1, the gel carrier 60 is set on support rest 52 and is positioned in such a manner that the center of fractionated patterns of a first specimen coincides with the optical axis of projector 44-receiver 45. Then, motor 57 is driven and photometry apparatus scans in the direction y, during which the density distribution of fractionated patterns for the first specimen is detected. Thereafter, motor 64 is driven to scan support rest 52 by a given interval of blood serum applications in the direction x. When the density distributions of all fractionated patterns for a specified number of specimens are detected, cover 46 is opened and light receiver 45 is lifted to take out the gel carrier 60. In the densitometer 40, in which the gel carrier 60 is half-manually positioned, a gel carrier may be positioned by a specimen detection means similar to the one used in positioning of the cellulose acetate carrier 1. In this case, if the specimen detection means is incorporated into the photometry apparatus 56 including light projector 44, light receiver 45 and light flux transmitter 54, it may be used in common. In addition, while motor 64 which is a power source for support rest 52 is different from the one for rollers 43, a power source for driving both carrier supporters may be in common through a suitable transfer means. In this case, if support rest 52 is previously disconnected from guide rail 62 during the measurement of the cellulose acetate carrier 1, there is no case that support rest 52 is driven beyond the limits of movement.

The support rest 52 is constructed to be driven in the direction x by means of a driving means including rack 52b, pinion 63 and motor 64. In case a specimen on the gel carrier 60 is limited to one, the support rest 52 may be fixed to a stationary member such as clearing liquid vessel 42 with a suitable means and thus the driving means may be eliminated.

While the case that a gel carrier 60 is to be set on support rest 52 is shown in the foregoing, it is not limited thereto. Specifically, if a carrier which is a cellulose acetate film which is previously cleared or a transparent carrier is used, the density distribution of a specimen on the carrier may be detected. It is also possible to conduct the measurement using a carrier film officially approved by the Electrophoresis Society which is generally used in Japan for authorization of measured values by a densitometer.

Figure 7:
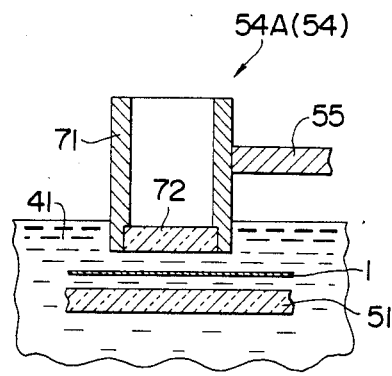
FIGS. 7 to 9 are cross sections showing respective examples of a light flux transmitter shown in FIGS. 5 and 6.
Figure 8:
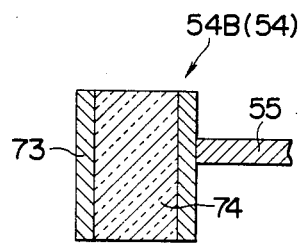
Figure 9:
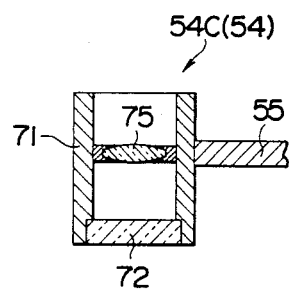

In FIGS. 7 to 9, there are shown cross sections of various light flux transmitters 54. The transmitter 54A in FIG. 7 has a cylindrical frame 71 whose bottom is covered with a glass plate 72 and even though the liquid surface of clearing liquid 41 is disturbed, light flux from light projector 44 may not be curved as the bottom of frame 71 is immersed in the clearing liquid 41. Light flux which is emitted from light projector 44 to light receiver 45 is preferably parallel but it is much difficult to obtain a completely parallel light flux as there generally occurs a slight spread. To restrain the spread of a light flux, a glass cylinder 74 which substantially fills the entire hollow portion of a light flux transmitter 54B in FIG. 8 so that light flux passing through glass cylinder 74 is substantially parallel and is transmitted to light receiver 45. Additionally, to prevent the spread of light flux in light flux transmitter 54A of FIG. 7, light flux transmitter 54C, as shown in FIG. 9, has a focusing lens 75 which is movably disposed within a cylinder frame 71 whose bottom is closed with a glass plate 72. Since the position of the cellulose acetate carrier 1 which is held by rollers 43 is different from the position of the gel carrier 60 which is held by support rest 52, the positioning of focusing lens 75 is adjusted to change a projection magnification so that fractionated patterns of a blood serum on either carrier may be focused on the light incident surface of light receiver 45, thereby good results of the measurement being obtainable. In general, it is preferred that a photometric spot image has a rectangular form whose long side is in the direction x so as to easily detect fractionated patterns shown in FIG. 2. To this end, the focusing lens 75 may be formed with a two directional zoom lens system which is independently variable in magnification in the directions x and y or an image guide.

In case the cellulose acetate carrier 1 which is previously cleared is fed into the densitometer 40, the clearing liquid 41 is unnecessary so that curving of light flux due to disturbance of the liquid surface is not caused and spreading of light flux from projector 44 toward light receiver 45 is not a matter of much concern. Therefore, in this case, it is to be noted that the light flux transmitter 54 (54A, 54B, 54C) may be eliminated.

What is claimed is:

1. A densitometer for an electrophoresis apparatus, comprising:
    a light projector for emitting light flux to detect the density distribution of fractionated patterns of a specimen to be examined after an electrophoresis process is completed;
    a light receiver for receiving the light flux from said light projector;
    a plurality of carrier supporter means disposed between said light projector and said light receiver for supporting carriers to which the specimen has been applied, after the electrophoresis process is completed; and
    scanning means for scanning said light projector and said light receiver at a station for detecting the specimen on said carrier which is supported by one of said carrier supporter means, in the direction along which fractionated patterns of said specimen are formed;
    the density distribution of fractionated patterns of said specimen on said carrier which is supported by one of said carrier supporter means being detected by an output of said light receiver.

2. A densitometer according to claim 1, in which said light projector and said light receiver are disposed upward and downward facing each other with said plurality of carrier supporter means arranged therebetween, one of said light projector and said light receiver which is located above the other being displace-able from a designated detecting station in such a manner that said one is easily movable to permit said supporter means to support the carrier.

3. A densitometer according to claim 1, in which said light receiver is adapted to removably mount a filter of the optimum wavelength in accordance with items to be analyzed while in the density measurement of fractionated patterns of a specimen.

4. A densitometer according to claim 1, in which said plurality of carrier supporter means are moved by drive means in order to successively detect fractionated patterns for a plurality of specimens which are applied to the carrier.

5. A densitometer according to claim 1, in which said plurality of carrier supporter means include a first and a second carrier supporter, said first supporter being formed of rollers between which a carrier formed of a flexible film is held and transferred to a station between said light projector and said light receiver to hold it thereat and said second supporter being formed of a support rest for mounting and holding a carrier formed of a suitable material at a level different from said first supporter and between said light projector and said light receiver.

6. A densitometer according to claim 5, in which said support rest is removably mounted on a guide rail which is arranged horizontally so as to enable the support rest to be driven by a rack which is formed as an integral part of said support rest, a pinion which engages with said rack and a motor which drives said pinion.

7. A densitometer according to claim 5, further including a light flux transmitter disposed in the optical path between said light projector and said light receiver for stabilizing a light flux, the bottom of said light flux transmitter being immersed in a clearing liquid for clearing a carrier formed of a flexible film.

8. A densitometer according to claim 7, in which said light flux transmitter has a cylindrical frame whose bottom end is fitted with a transparent plate formed of glass or the like.

9. A densitometer according to claim 7, in which said light flux transmitter has a hollow cylindrical frame into which a transparent member such as glass is fitted, said member filling substantially the entire interior of said frame.

10. A densitometer according to claim 7, in which said light flux transmitter has a cylindrical frame whose bottom is fitted with a transparent plate such as glass and within which the focusing lens for changing a projection magnification on the light incident surface of said light receiver is arranged.

11. A densitometer according to claim 7, in which said light flux transmitter is moved by said scanning means in unison with said light projector and said light receiver.

* * * * *